United States Patent [19]

Kamens et al.

[11] Patent Number: 4,567,899
[45] Date of Patent: Feb. 4, 1986

[54] CUFF PRESSURE CONTROLLER FOR BLOOD PRESSURE MEASUREMENT APPARATUS

[75] Inventors: Bruce H. Kamens, Thomaston; Paul Wuthrich, Watertown; Jacob Fraden, Hamden, all of Conn.

[73] Assignee: Healthcheck Corporation, Cheshire, Conn.

[21] Appl. No.: 635,994

[22] Filed: Jul. 30, 1984

[51] Int. Cl.⁴ .............................................. A61B 5/02
[52] U.S. Cl. ..................................... 128/680; 128/685
[58] Field of Search ............... 128/672, 677, 680–686

[56] References Cited

U.S. PATENT DOCUMENTS

| | | | |
|---|---|---|---|
| 3,905,354 | 9/1975 | Lichowsky | 128/681 |
| 4,011,860 | 3/1977 | Lee | 128/683 |
| 4,252,127 | 2/1981 | Gemelke | 128/683 X |
| 4,295,471 | 10/1981 | Kaspari | 128/675 |
| 4,312,359 | 1/1982 | Olson | 128/680 |
| 4,313,445 | 2/1982 | Georgi | 128/680 |
| 4,326,536 | 4/1982 | Kitagawa et al. | 128/682 |
| 4,328,810 | 5/1982 | Hill et al. | 128/680 |
| 4,343,314 | 8/1982 | Sramek | 128/683 X |
| 4,378,807 | 4/1983 | Peterson et al. | 128/677 |
| 4,464,123 | 8/1984 | Glover et al. | 128/681 X |

FOREIGN PATENT DOCUMENTS 2087238  5/1982  United Kingdom ............... 128/680

Primary Examiner—Lee S. Cohen
Assistant Examiner—Angela D. Sykes
Attorney, Agent, or Firm—William C. Crutcher

[57] ABSTRACT

A blood pressure measurement instrument controlled by a microprocessor has an inflatable cuff, a pump for inflating the cuff, an acoustic sensor and amplifier for processing auscultatory sounds and supplying signals to a microcomputer, a display for displaying blood pressure, and pressure sensor for measuring air pressure in the cuff and supplying signals to the microprocessor. The invention comprises an improved air bleed rate controller for providing a linearized bleed slope reference signal which is compared to an actual cuff pressure signal from the cuff pressure transducer, to control a variable opening bleed valve. The reference signal is applied at the initiation of the bleed control phase through a logic circuit from the microcomputer and a time delay switch. Additional logic provides a bleed valve override signal for closing the valve during the pumping phase and providing dumping of cuff pressure on the completion of blood pressure measurement.

10 Claims, 7 Drawing Figures

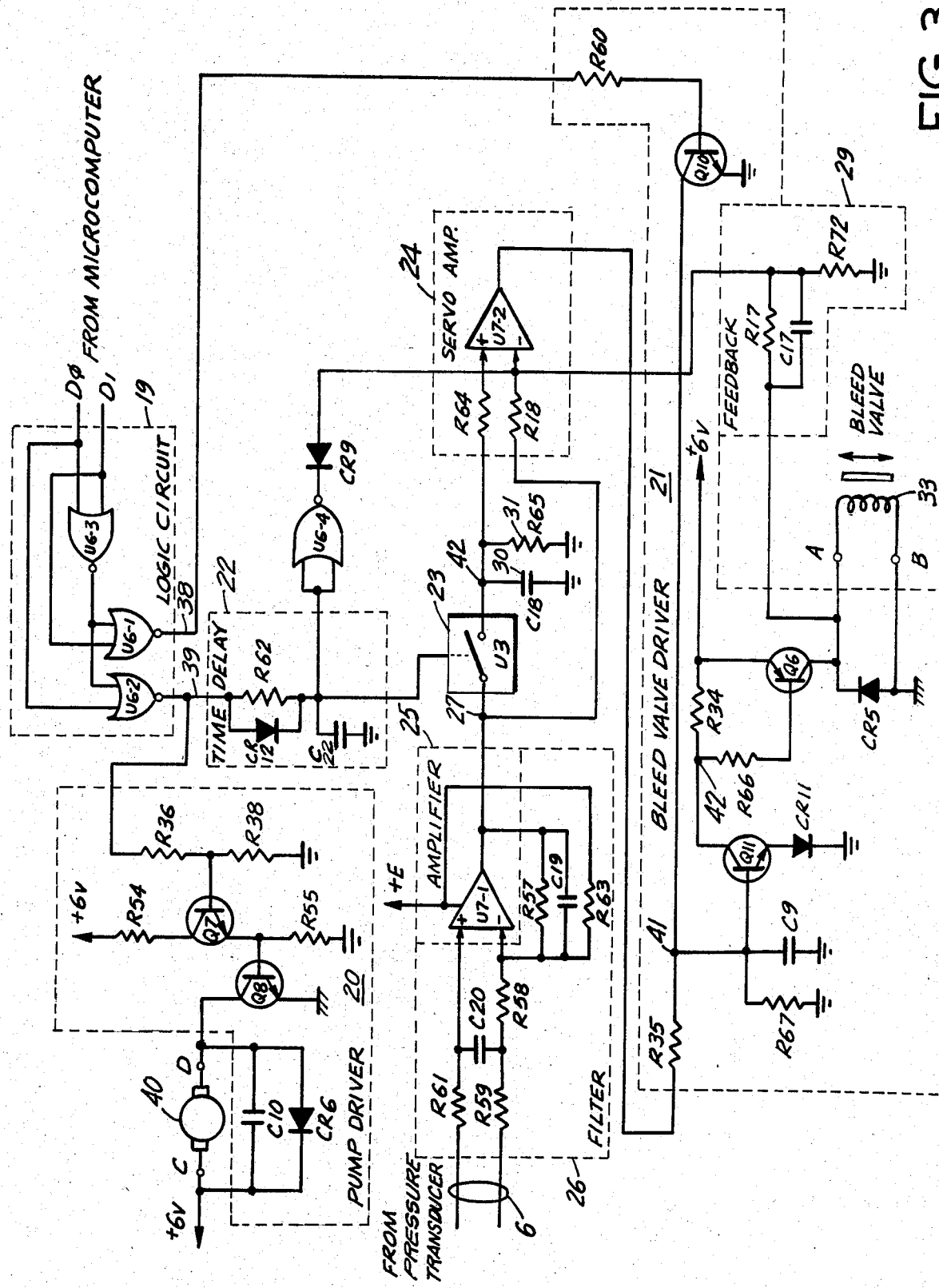

CUFF PRESSURE CONTROLLER FOR BLOOD PRESSURE MEASUREMENT APPARATUS

BACKGROUND OF THE INVENTION

This invention relates to blood pressure measurement apparatus, and more particularly to an improved cuff pressure controller for such apparatus.

Blood pressure measurement apparatus is known of the type wherein auscultatory (Korotkoff) sounds are detected as the air pressure is bled from an inflatable cuff, in order to determine the systolic and diastolic pressures and to display them. Such apparatus has been improved by substituting automatic inflation and deflation of the cuff for the conventional manual squeeze bulb and manual bleed valve. Examples of such blood pressure measurement devices and techniques are illustrated by U.S. Pat. No. 4,328,810—Hill et al. This patent illustrates the blood pressure measurement device with a controller for a pump to inflate the cuff and a solenoid valve to bleed the cuff under proportional control, using a constant frequency variable duty cycle arrangement. Hill employs a pulse train and varies the duty cycle to maintain a constant deflation rate by comparing the actual rate of change of pressure and the desired rate of change of pressure.

U.S. Pat. No. 4,313,445 issued Feb. 2, 1982 to Georgi similarly illustrates a computer controlled blood pressure measurement apparatus measuring Korotkoff sounds to determine blood pressure during controlled decrease of cuff pressure by automatic bleeding of air from the cuff under computer control.

U.S. Pat. No. 4,326,536 issued to Kitagwa et al. on Apr. 27, 1982 shows an automatic pumping, pressure bleeding and pressure dumping control for an auscultatory sphygmomanometer, wherein bleeding of pressure is regulated by a mechanical diaphragm-controlled slow exhaust valve, with solenoid coil to close the valve during an intermittent pumping cycle.

U.S. Pat. No. 4,295,471—Kaspari issued Oct. 20, 1981 discloses apparatus for automatically inflating and deflating a cuff, with a pressure transducer measuring cuff pressure, and suggests bleeding cuff pressure at a reduced rate during one part of the cycle and at a higher rate during other parts of the cycle.

U.S. Pat. No. 4,312,359—Olson issued Jan. 26, 1982 controls the cuff deflation by opening a pressure relief valve for short periods of time on an intermittent basis.

U.S. Pat. No. 3,905,354—Lichowsky issued Sept. 16, 1975 employs proportional valves to admit fluid under pressure to inflate the cuff and to bleed fluid pressure from the cuff, seeking to produce a substantially linear cuff pressure decrease in response to pressure rate-of-change feedback signals from a differentiating circuit.

British Application GB No. 2 087 238A discloses an automatic pumping and depressurizing device under control of a microprocessor, programmed to provide a signal which linearly decreases the pressure by opening and closing solenoid valves.

Lastly, U.S. Pat. No. 4,378,807 to Peterson et al. issued Apr. 5, 1983 shows an automatic cuff pressurizing and depressurizing system for a blood pressure measurement device of the type described, in which pressure lamp linearization circuits are employed. A decreasing pressure ramp reference signal is produced by discharging a capacitor through a constant current source to provide a negative-going ramp. A difference amplifier compares the reference voltage with actual voltage sent by a pressure transducer, and controls off-on valves with width modulated pulses. The modulator valve bleeding the cuff is therefore opened and closed for different periods of time, depending upon deviation in the cuff pressure from the generated reference ramp.

One of the disadvantages in the Peterson et al. patent with the use of off-on valves controlled using a variable duty cycle is that the off-on operation of the valves may create electrical noise through the power supply and acoustic noise generated by valve opening and closing. This noise may interfere with the Korotkoff sound detection. It would be desirable to have a cuff pressure bleed rate control device which provides a substantially linear pressure decrease with minimum electrical and acoustic noise generation to interfere with the readings.

It would also be desirable to provide an improved cuff pressure controller having a simplified circuit to generate substantially linear, decreasing, pressure reference signal. Such an improved cuff pressure controller circuit would include provision for initial inflation of the cuff, initialization of bleeding air from the cuff after reaching a desired pressure, controlled bleed rate during measurement, and termination of the deflation/measurement phase by dumping pressure from the cuff as quickly as possible.

Accordingly, one object of the present invention is to provide an improved cuff pressure controller for an auscultatory blood pressure measurement device.

Another object of the present invention is to provide an improved cuff pressure automatic controller for a microcomputer-controlled blood pressure measurement device, which controls inflation, bleed, and dumping of the cuff.

Still another object of the invention is to provide an improved circuit for controlling a bleed valve during depressurization of a cuff with minimum acoustic and electrical noise.

These and other objects of the invention will best be understood by reference to the following description, taken in connection with the accompanying drawings, in which:

FIG. 1 is a simplified block diagram of a blood pressure measurement apparatus employing the invention, FIG. 2 is an elevation drawing, partly in section of one type of variable opening valve used with the present invention, FIG. 3 is an electrical circuit diagram of the essential elements of the blood pressure controller used in the blood pressure measurement apparatus, FIGS. 4a–4d, are graphs showing electrical quantities plotted against a time scale, in order to illustrate operation of the invention.

SUMMARY OF THE INVENTION

Briefly stated, the invention is practiced by providing in a blood pressure measurement apparatus of the type having an inflatable blood pressure cuff, a pressure transducer for measuring pressure in the cuff, a pump for inflating the cuff, and a microcomputer controlled means for measuring and processing auscultatory sounds and displaying diastolic and systolic blood pressure during decreasing pressure in the cuff, an improved cuff pressure controller for inflating the cuff, bleeding pressure from the cuff at a substantially linear discharge rate using a variable opening valve, and dumping cuff pressure at the completion of blood pressure measurement. In its preferred embodiment, the bleed rate controller utilizes a pressure transducer to obtain a filtered signal proportional to cuff pressure, which signal is applied to one input of an operational amplifier and is also applied as a reference signal to the other input of the operational amplifier through an analog switch, having interposed between the switch and the amplifier a capacitor which is charged to an initial reference signal corresponding to actual pressure when the switch is closed.

Also connected in circuit with the switch and the amplifier are means to discharge the capacitor at a substantially linear rate when the switch is opened. A logic circuit is provided to operate the pump, control the opening of the analog switch with a time delay, and provide a bleed valve overriding signal to fully open the valve, in response to signals from the miroprocessor.

DESCRIPTION OF THE PREFERRED EMBODIMENT

Figure 1:
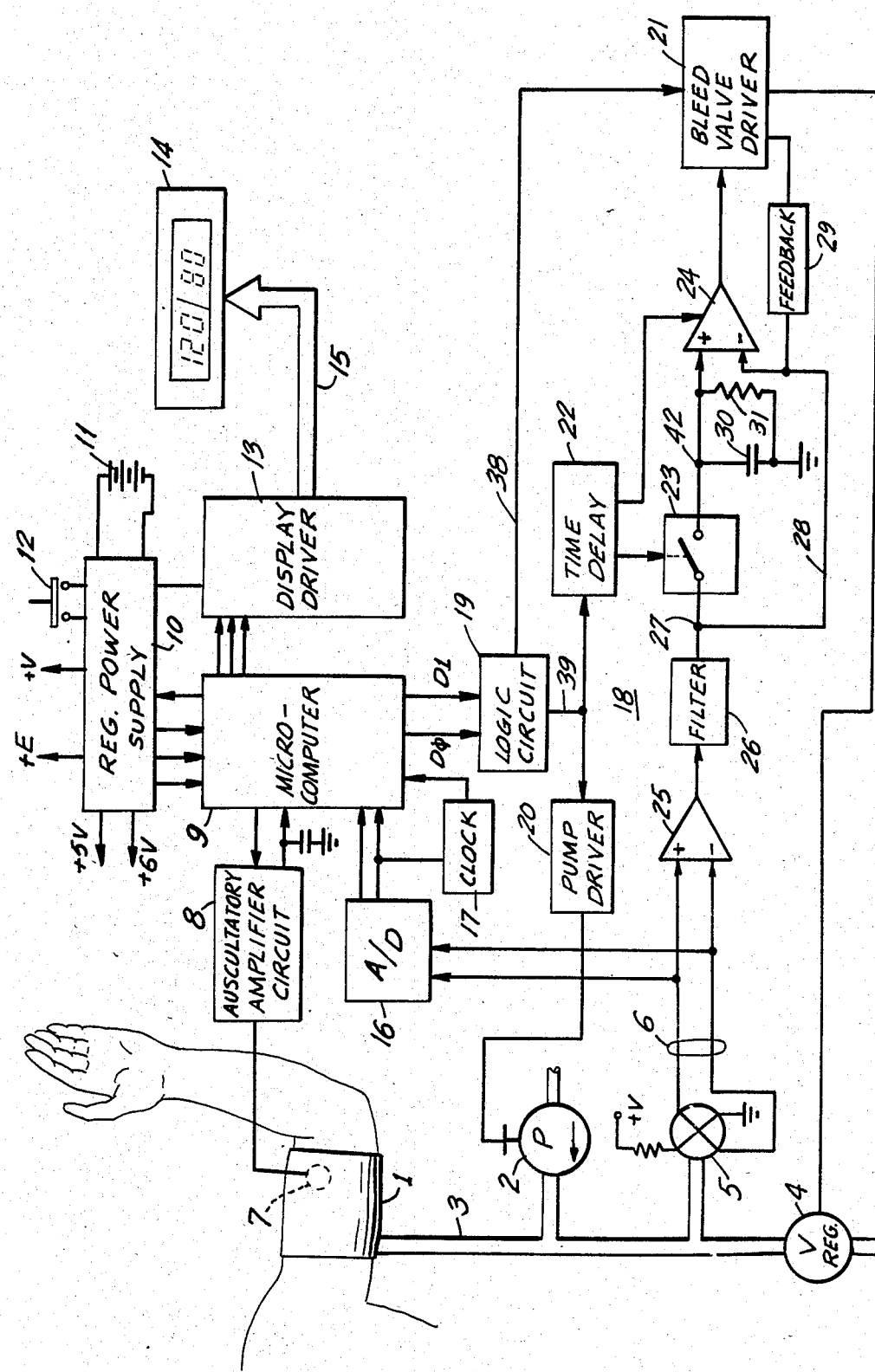

Referring now to FIG. 1 of the drawing, the blood pressure measurement apparatus shown in simplified block diagram includes an inflatable blood pressure cuff 1 having a pump 2 connected to pressurize a hose 3 leading to the cuff and a variable opening bleed valve 4 connected to bleed air pressure from the hose 3. A pressure transducer 5 is also connected to hose 3 to provide a variable analog voltage over leads 6 which is proportional to the air pressure in cuff 1. Pressure transducer 5 may be a commercially available transducer, such as Model MPX500 manufactured by Motorola, which incorporates a strain gauge bridge responsive to changes in cuff pressure.

Cuff 1 contains a crystal microphone 7 positioned over the brachial artery connected to an auscultatory amplifier circuit 8 which, in turn, is connected to a microcomputer 9. The details of circuit 8 are not material to the present invention, but the circuit may be one as more fully disclosed in copending application, Ser. No. 398,050 filed July 14, 1982 in the name of Jacob Fraden and assigned to the present assignee. In that application, an electronic sphygmomanometer is disclosed that accurately measures systolic and diastolic blood pressures using two thresholds; a first fixed threshold for determining systolic pressure and a second floating threshold for determining the diastolic pressure. The first threshold is fixed somewhat above the highest noise amplitudes generated while the pressure cuff is inflated above the point of occluding the underlying artery. The noise includes the auscultatory sounds produced in the artery and detected by the microphone. The second floating threshold is produced based on the peak auscultatory sounds as the pressure cuff is deflated. A computer, such as the microcomputer 9, provides the correspondence between the cuff pressure and the simultaneously occurring first auscultatory sound detected with respect to the first threshold level after the cuff begins to deflate for determining and displaying systolic blood pressure. Similarly, the diastolic blood pressure is determined and displayed when the last auscultatory sound detected with respect to the second floating threshold level corresponds to a simultaneously detected cuff pressure.

A regulated power supply 10 provides a number of regulated output voltage levels necessary to operate the blood pressure measurement apparatus from a voltage source, such as battery 11, in response to a power-on switch 12. Microcomputer 9 is associated with a display decoder and driver 13 connected to a liquid crystal display 14 by a bus 15. Microcomputer 9 and decoder/driver 13 are commercially available devices, such as COP-421 and COP-472 manufactured by National Semiconductor. The microcomputer 9 may be provided with a program in a read-only-memory section of the microcomputer, in a manner known in the art, to respond to various conditions in the blood pressure measurement apparatus, to provide various signals from its output ports over leads such as D0 and D1, and to provide signals to the decoder/driver for display on the liquid crystal display 14. Other inputs to microcomputer 9 serve to monitor cuff pressure. The analog voltage on leads 6 corresponding to the cuff air pressure is converted to digital form in an analog-to-digital converter 16. A clock signal is provided to operate the microcomputer by a clock circuit 17, which may be a relaxation oscillator.

In accordance with the present invention, the inflation of the pressure cuff, the controlled bleed down of the pressure cuff while blood pressure measurements are computed, and dumping of the pressure from the cuff at the conclusion of the blood pressure measurement are carried out by a cuff pressure controller, shown generally at 18. Controller 18 is taken through various stages of operation in response to signals from a logic circuit 19 which, in turn, is responsive to signals from the microcomputer over output leads D0 and D1. Logic signals from logic circuit 19 directly control the operation of pump 2 and valve 4 through a pump driver circuit 20 and a linear bleed valve driver circuit 21, respectively. Logic signals from the logic circuit 19 are supplied via a time delay circuit 22 to an analog switch 23 and a servo amplifier 24.

The analog voltages on lead 6 are compared at the inputs of an operational amplifier 25, which may be incorporated in circuit with a low pass filter 26 to remove high frequency electrical noise from the bleed valve control circuit. A filtered voltage or first signal free of high frequency noise corresponding to actual cuff pressure is supplied by amplifier 25 and filter 26 to a junction 27 connected to one side of an analog switch 23. The other side of analog switch 23 at junction 42 is connected to the non-inverting input of operational amplifier 24, which has its output connected to bleed valve driver circuit 21. The non-inverting input of operational amplifier 24 is also directly connected to junction 27 via lead 28, and through a feedback circuit 29 to the bleed valve circuit 21.

In accordance with one aspect of the present invention, a capacitor 30 is connected to junction 42 between analog switch 23 and the non-inverting input of amplifier 24, in order to provide a bleed valve controlling ramp reference voltage or reference signal when switch 23 is open. Capacitor 30 is connected on the other side to ground. Circuit means for discharging capacitor 30 comprises a resistor 31 connected in parallel with capacitor 30.

Figure 2:
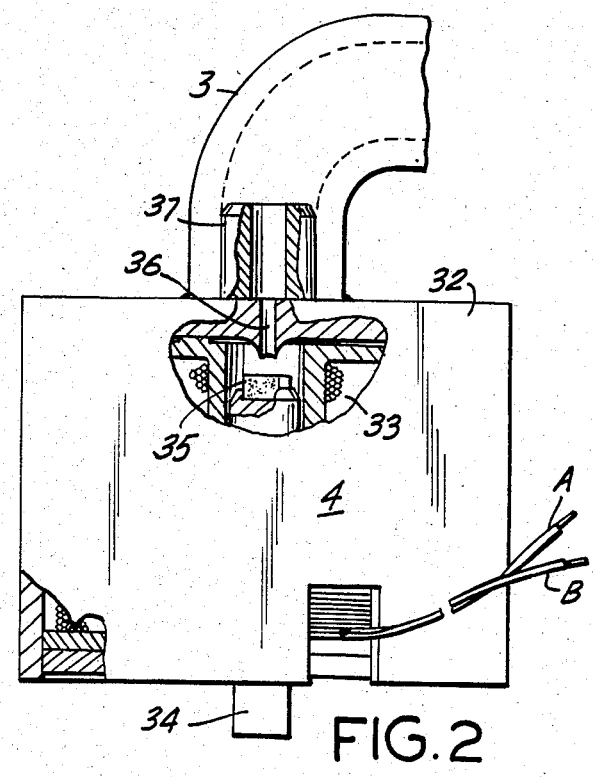

Referring now to FIG. 2 of the drawing, a variable opening valve 4 suitable for practicing the present invention is shown in greater detail. A valve body 32 houses a solenoid coil 33 with leads A, B. A moveable solenoid plunger 34 is adapted to move vertically upward in response to increasing current in coil 33. Plunger 34 could be spring biased, but in the preferred embodiment is simply biased downward by gravity when the valve is in the position shown in the drawing. Plunger 34 has a seal 35 on its upper end which is adapted to cooperate with a flow control orifice 36 to form a variable opening. Orifice 36 is connected via a fitting 37 to the hose 3 communicating with the cuff. The operation of the valve is such that a greater magnitude of current flowing through coil 33 produces a greater constriction of the air escaping from orifice 36, so that the rate of bleed of air pressure from hose 3 can be varied by controlling the current in the coil. A predetermined current magnitude in the coil will completely close the orifice 36 and prevent escape of air from the hose; the valve is fully open to dump the cuff pressure when no current flows in coil 33. The construction of the valve with only one moving part and no springs serves to vary the orifice opening with minimum mechanical sound disturbances, which might interfere with reading of the blood pressure auscultatory sounds.

Referring now to FIG. 3 of the drawing, the circuit details are shown for certain boxes in the schematic view of FIG. 1 which are germane to the present invention. The portions of the circuit enclosed within dashed lines are labeled with reference numbers corresponding to the blocks shown in FIG. 1.

Logic circuit 19 includes NOR devices U6-1, U6-2, and U6-3 connected to decode signals on lines D0 and D1 from the microprocessor. Combinations of signals on D0, D1 control three phases of operation of the blood pressure measurement apparatus by causing selected low or high outputs on leads 38, 39 comprising logic signals from the logic circuit. The logic connections are such that the three phases of control: inflation of the cuff, bleeding the cuff, and dumping pressure from the cuff are accomplished in accordance with the following table.

TABLE 1

| D0 | D1 | 38 | 39 | PHASE |
|---|---|---|---|---|
| 1 | 0 | LOW | HIGH | INFLATE CUFF |
| 0 | 0 | LOW | LOW | BLEED CUFF |
| 0 | 1 | HIGH | LOW | DUMP CUFF PRESS. |

The pump driver 20 includes an NPN control transistor Q7, and an NPN power transistor Q8 having its emitter and collector connected in circuit with terminals C, D of a pump motor 40, driving pump 2 shown in FIG. 1. The base of transistor Q8 follows the emitter of transistor Q7 to turn on the pump when the base of Q7 goes positive by placing a high signal on lead 39 from the logic circuit.

A signal from lead 39 is also applied to the time delay circuit 22 which comprises resistance R62 and capacitor C22. A diode CR12 is connected across resistor R62 in such a manner that when signal on lead 39 goes from low to high, the time delay resistor R62 is bypassed. However, when the signal on lead 39 goes from high to low, it is delayed in accordance with component values selected for R62 and C22. The preferred time constant of the RC circuit is approximately 2 seconds. The output signal from time delay circuit 22 is applied as a control signal to analog switch 23, a high signal serving to close the switch, and a low signal serving to provide a (delayed) opening of the switch. The time delayed signal from circuit 22 is also applied to both inputs of NOR device U6-4 to invert the signal. The output lead of U6-4 is connected through diode CR9 to the inverting input of amplifier 24.

Voltages from the pressure transducer are input over leads 6 to an operational amplifier 25 arranged to incorporate a low pass filter 26. A first input circuit R58, R59, R61, and C20 is connected to the input of an operational amplifier U7-1. A second filter component is provided by C19 which is connected from the output to the inverting input of amplifier U7-1 to limit high frequency gain. A small biasing current is supplied through resistor R63 to the inverting input, which provides compensation for the offset voltage of the transducer and keeps the output from amplifier U7-1 from rising above a predetermined value. The RC input circuit and RC feedback circuit together operate as a low pass filter to remove high frequency electrical noise from the voltage output of amplifier 25 which will be porportional to cuff pressure above the offset value. This voltage or first signal is applied to junction 27.

The bleed valve servo amplifier 24 comprises an operational amplifier U7-2 having input resistors R64 and R18 connected to junction 42 at the output of analog switch 23 and to junction 27 at the input of analog switch 23 respectively.

A first override control signal may be provided through first circuit means, comprising a NOR U6-4 connected as an inverter and diode Cr9 connected between the output of time delay circuit 22 and the inverting input of amplifier 24. A high signal at the time delay output clamps the non-inverting input of U7-2 to ground potential. Therefore, a signal on the other input of amplifier U7-2 will fully close the bleed valve.

The bleed valve driver circuit, indicated within dashed lines 21, includes an input resistor R35 connected to the base of an NPN transistor Q11, which in turn is connected to ground through a parallel-connected capacitor C9 and resistor R67. The emitter of Q11 is connected to ground via a diode CR11, while the collector is connected to a voltage source via resistor R34. A second PNP transistor Q6 has a base connected via resistor R66 to a junction 42 between R34 and Q11. The emitter of Q6 is connected to the voltage source and the collector is connected to one side of solenoid coil 33. The other side of solenoid coil 33 is connected to ground. The operation is such that a high signal applied to input resistor R35 serves to turn on transistor Q11, which in turn biases the base of transistor Q6 to turn it on and control current in the solenoid coil 33, which current is responsive to the magnitude of the output voltage from amplifier 24.

A second override control signal is provided through second circuit means to fully open the bleed valve when logic signal on lead 38 from the logic circuit goes high. Lead 38 is connected via resistor R60 to the base of an NPN transistor Q10. The emitter of Q10 is connected to ground, while the collector is connected to the junction 41 between R35 and the base of transistor Q11. A high signal on lead 38 will turn on transistor Q10 and cause junction 41 to fall to ground potential. This in turn turns off Q11, Q6, to shut off current in solenoid coil 33, allowing the bleed valve to open fully.

Table 2 shows representative values of passive circuit components in FIG. 3, as well as commercial model numbers for the active components.

TABLE 2

| | |
|---|---|
| R17 - 2.2 M | CR5 - 1N914 |
| R18 - 100K | CR6 - 1N4001 |
| R34 - 22K | CR9 - 1N914 |
| R35 - 10K | CR11 - 1N914 |
| R36 - 4.3K | CR12 - 1N914 |
| R38 - 120K | |
| R54 - 43 ohms (¼ W) | C9 - 10.0 |

TABLE 2-continued

| | |
|---|---|
| R55 - 4.7K | C10 - .01 |
| R57 - 680K | C17 - 0.1 |
| R58 - 5.6K | C18 - 100.0 |
| R59 - 5.6K | C19 - 0.1 |
| R60 - 120K | C20 - 0.1 |
| R61 - 10K | C22 - 1.0 |
| R62 - 2.2 M | |
| R63 - 2.7 M | |
| R64 - 100K | Q6 - 2N4403 |
| R65 - 820K | Q7 - 2N4401 |
| R66 - 330 ohms | Q8 - 2N5190 |
| R67 - 120K | Q10 - 2N4401 |
| R72 - 5.1 M | Q11 - 2N4401 |
| U3-CD4066  U6-CD4001 | U7-LM324AN |

Figure 4A:
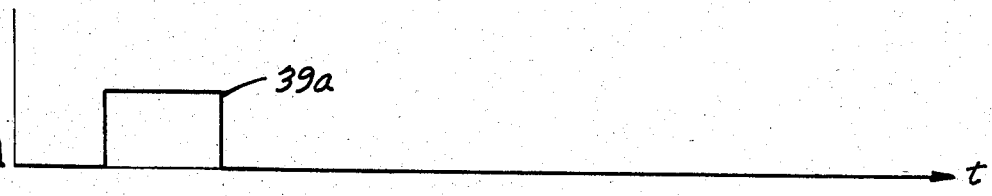
Figure 4B:
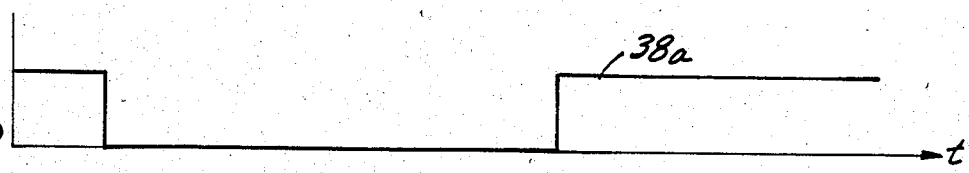
Figure 4C:
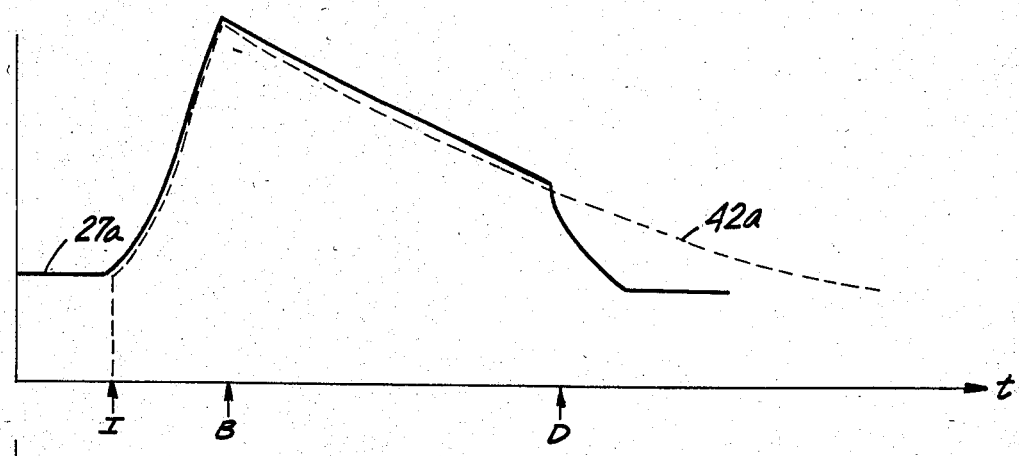
Figure 4D:
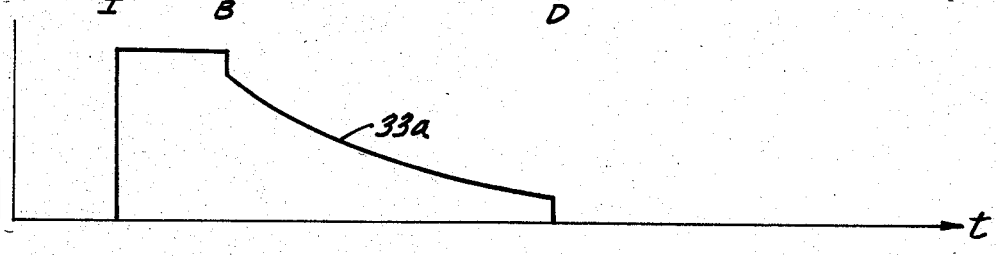

FIGS. 4a–4d illustrate the various parameters in the control system plotted against a time scale. FIG. 4a shows the logic signal 39a applied on output lead 39. FIG. 4b illustrates the logic signal 38a applied to lead 38. In FIG. 4c, curve 27a illustrates the first signal supplied at the output of amplifier 25 to the junction 27, which is representative of actual cuff pressure. The second curve 42a is the reference signal appearing at junction 42, which is applied as a reference signal to control the bleed valve amplifier 24. Finally, curve 33a in FIG. 4d represents the current flowing through the solenoid coil 33 of the bleed valve.

OPERATION

The operation of the invention will now be described by reference to the block diagram of FIG. 1, Table 1 in the specification, and the graphs of FIGS. 4a–4d.

At the start of the inflation cycle (point "I" on FIG. 4c), logic signal 38a on control lead 38 from the logic circuit 19 goes low and logic signal 39a on lead 39 goes high. A high signal on lead 39 starts the pump 2 by turning on the pump driver circuit to pump motor 40, closes the analog switch 23 so that the voltage applied to junctions 27, and 42 leading to the inputs of servo amplifier 24 are the same. This causes servo amplifier 24 to saturate with output high, and to attempt to close the bleed valve all the way. A low signal on lead 38 turns off transistor Q10 (FIG. 3) which allows the amplifier to close the bleed valve. As the cuff pressure increases, capacitor 30 charges and the voltage at junctions 27, 42 increases exponentially as shown by curves 27a, 42a in the graph. Full current flows through the valve solenoid as indicated by the graph curve 33a.

The microcomputer is programmed so that when a predetermined cuff pressure is reached, as sensed by the pressure transducer 5 and communicated to the microcomputer by A/D converter 16, low signals are output over both leads D0 and D1 respectively to the logic circuit 19. This initiates the second or bleed phase of operation.

The second phase of operation (point "B" on FIG. 4c) commences when the logic signal 39a on lead 39 goes low. When the signal on lead 39 goes low, the pump is stopped, the analog switch 23 is opened, and the inverting input of amplifier 24 is unclamped after a time delay determined by time delay circuit 22. The time delay before switch 23 is opened permits the pump to stop and the battery voltage to stabilize before the switch is opened. When the switch 23 is opened, the voltage at junction 42 becomes the reference signal for amplifier 24 which is now in a pressure controlling mode. The reference signal varies the orifice opening of the variable opening valve, so that the actual pressure signal at junction 27 will attempt to match the signal at reference junction 42. The potential at junction 42 decays along a substantially linear ramp as indicated by graph line 42a, while the actual pressure, indicated by 27a, is controlled along the same ramp. It will be understood by those skilled in the art that the bleed ramp is not exactly linear, but corresponds to an exponential decay curve, determined by the selected values of capacitor 30 and resistor 31. However, the values of the components are selected so that, over the range of interest, the ramp is substantially linear. An exactly linear negative ramp could be provided by substituting a current source for resistor 31, and this substitution is within the scope of the present invention.

The third phase of operation (Point "D" on FIG. 4d) begins when the signal 38a on lead 38 goes high, turning on transistor Q10 which shuts off current to coil 33 allowing the bleed valve to fully open. This signal overrides any valve positioning signal from amplifier 24. The pressure is released from the cuff, as indicated by the curve 27a. The signal curve will not fall below a minimum value, but the actual pressure in the cuff is quickly reduced to ambient pressure so that the cuff can be removed.

While there has been disclosed what has been considered to be the preferred embodiment of the invention, other modifications will occur to those skilled in the art, and it is desired to secure in the appended claims all such modifications as fall within the true spirit and scope of the invention.

We claim:

1. In a blood pressure measurement apparatus including an inflatable blood pressure cuff, a pump means for pressurizing said cuff, a pressure transducer continuously providing a voltage signal proportional to the pressure in said cuff, means including an acoustic detector, auscultatory amplifier, and microcomputer means for detecting auscultatory sounds and computing blood pressure corresponding to cuff pressure, an improved cuff pressure controller comprising:
   a variable opening valve connected to bleed air from said blood pressure cuff,
   first amplifier means connected to said pressure transducer to provide a first signal representative of actual cuff pressure,
   reference circuit means including (1) a capacitor connected with means to discharge said capacitor for providing a substantially linearly decreasing reference signal and (2) an analog switch responsive to logic signals from said microcomputer means, said switch being connected to the output of said first amplifier means, so as to charge the capacitor with said first signal when the switch is in a first state and to allow the capacitor to discharge for supplying said decreasing reference signal when the switch is in a second state, and
   second amplifier means connected to said reference circuit means and which continuously varies the opening of said variable opening valve in response to said reference signal, so as to cause the actual cuff pressure to follow the decreasing reference signal when bleeding pressure.

2. The combination according to claim 1, wherein said first amplifier means is a low pass amplifier arranged to filter high frequency electrical noise from said first signal.

3. The combination according to claim 1, wherein the means to discharge said capacitor is a parallel-connected resistance, selected to provide a substantially linear decrease of the reference signal while blood pressure is computed by the microcomputer means.

4. The combination according to claim 1, including a logic circuit means connected to the microcomputer means and providing a plurality of logic signals cuff for sequentially operating said pump means and closing said valve to inflate the cuff, opening said switch to bleed the cuff with the variable opening valve, and fully opening the valve to dump pressure from the cuff.

5. The combination according to claim 4, including a time delay circuit connected between said logic circuit means and said analog switch, whereby the logic signal opening said switch is delayed for a preselected time prior to opening said switch.

6. The combination according to claim 4, including first circuit means connected between the logic circuit means and said second amplifier means for causing the second amplifier means to close said valve, said first circuit means, said pump means, and said analog switch all being responsive to a logic signal from said logic circuit means whereby the pump means is started, the valve is closed, and the switch is closed to commence inflation of the cuff.

7. The combination according to claim 4, wherein said valve is arranged to open in the absence of a signal and including second circuit means connected between the logic circuit means and said second amplifier means for disabling the second amplifier means and allowing the valve to open, regardless of the value of said reference signal, whereby a logic signal applied to the second circuit means will dump pressure from the cuff.

8. The combination according to claim 1, wherein said valve has a solenoid coil arranged to actuate a vertically moveable plunger, said plunger varying the opening in a fixed orifice connected to said inflatable cuff, said plunger being gravity-biased to open the orifice when current does not flow in said coil.

9. The combination of claim 1, wherein said microcomputer means is programmed to stop the pump means and to initiate opening of said analog switch in response to a predetermined cuff pressure measured by said transducer.

10. In a blood pressure measurement apparatus including an inflatable blood pressure cuff, a pump means for pressurizing said cuff, a pressure transducer continuously providing a voltage signal proportional to the pressure in said cuff, means including an acoustic detector, auscultatory amplifier, and microcomputer means for detecting auscultatory sounds and computing blood pressure corresponding to cuff pressure, an improved cuff pressure controller comprising:

a variable opening solenoid valve connected to bleed air from said blood pressure cuff, said valve opening fully when current is not supplied to the valve, first low pass amplifier means connected to said pressure transducer to provide a first signal representative of actual cuff pressure with high frequency noise filtered from said first signl, reference circuit means including (1) a capacitor connected with a resistor which discharges said capacitor for providing a substantially linearly decreasing reference signal and (2) an analog switch responsive to logic signals from said microcomputer means, said switch being connected to the output of said first amplifier means, so as to charge the capacitor with said first signal when the switch is closed and to allow the capacitor to discharge when the switch is open, second amplifier means connected to said reference circuit means and for continuously varying the opening of said variable opening valve in response to said reference signal, so as to cause the actual cuff pressure to follow the decreasing reference signal when bleeding pressure, said second amplifier means including first circuit means for causing the second amplifier means to close the valve when said first circuit means is enabled, and second circuit means connected to disable the second amplifier means when said second circuit means is enabled to shut off current to said valve and to allow the valve to open regardless of the value of said reference signal, and a logic circuit means connected to the microcomputer means and providing a plurality of signals for sequentially (1) starting said pump, closing said analog switch, and enabling the first circuit means, (2) stopping said pump, opening said switch, and disabling the first circuit means, and (3) enabling the second circuit means.

* * * * *